(12) United States Patent
Cid Vivanco et al.

(10) Patent No.: US 8,715,747 B2
(45) Date of Patent: May 6, 2014

(54) BIOCOMPOSITION STIMULANT OF THE IMMUNE SYSTEM, ANTI-TUMOR AND ANTI-HIV

(75) Inventors: Roberto Cid Vivanco, Quito (EC); Renato Andrade Bejarano, Quito (EC)

(73) Assignee: Pharmabrand S.A., Quito (EC)

( * ) Notice: Subject to any disclaimer, the term of this patent is extended or adjusted under 35 U.S.C. 154(b) by 340 days.

(21) Appl. No.: 12/733,739

(22) PCT Filed: Sep. 18, 2008

(86) PCT No.: PCT/EC2008/000007
§ 371 (c)(1),
(2), (4) Date: Feb. 29, 2012

(87) PCT Pub. No.: WO2009/036772
PCT Pub. Date: Mar. 26, 2009

(65) Prior Publication Data
US 2012/0156247 A1    Jun. 21, 2012

(30) Foreign Application Priority Data
Sep. 21, 2007  (EC) ...................................... 07-7765

(51) Int. Cl.
*A61K 36/00*  (2006.01)

(52) U.S. Cl.
USPC ...................................................... 424/725

(58) Field of Classification Search
None
See application file for complete search history.

(56) References Cited

U.S. PATENT DOCUMENTS

| | | | | |
|---|---|---|---|---|
| 5,084,388 A | * | 1/1992 | Saimoto et al. | 435/124 |
| 2002/0081731 A1 | * | 6/2002 | Stafford et al. | 435/420 |
| 2004/0161524 A1 | * | 8/2004 | Sakai et al. | 426/655 |
| 2007/0122492 A1 | * | 5/2007 | Behr et al. | 424/725 |
| 2009/0104295 A1 | * | 4/2009 | Kohno | 424/757 |

OTHER PUBLICATIONS

Supratman, Unang et al., "Anti-tumor Promoting Activity of Bufadienolides from Kalanchoe pinnata and K. daigremontiana x tubiflora", Bioscience, Biotechnology and Biochemistry, 2001, pp. 947-949, vol. 65, No. 4.

Nohara, Toshihiro et al., "Physiological functions of solanaceous and tomato steroidal glycosides", Journal of Natural Medicines, 2007, pp. 1-13, vol. 61, The Japanese Society of Pharmacognosy and Springer-Verlag.

Antoun, M.D. et al., "Evaluation of the Flora of Puerto Rico for In Vitro Cytotoxic and Anti-HIV Activities", Pharmaceutical Biology, 1999, pp. 277-280, vol. 37, No. 4, Swets & Zeitlinger.

Araki, Shinako et al., "BIRM, an Andean Plant Extract, Down Regulates Androgen Receptor and Shows Anti-Tumor Activity in Prostate Cancer", Proceedings of the American Association for Cancer Research Annual Meeting, 2006, vol. 47.

Ren, J. et al., "Primary study on the anti-tumor effect of ethanol extracts of Solanum lyratum", China Journal of Chinese Materia Medica, 2006, pp. 497-500 (abstract), vol. 31, No. 6.

\* cited by examiner

*Primary Examiner* — Chris R Tate
(74) *Attorney, Agent, or Firm* — Nath, Goldberg & Meyer; Tanya E. Harkins (57) ABSTRACT

Provided is a herbal composition of plants obtained from non-domestic wild sources by means of meristems and the extracts thereof obtained using improved processes, in which the extracts and the active principles thereof generate a synergism demonstrating anti-inflammatory, antiviral nutritional supplement, immune system simulating, prostatic health promoting and supporting properties for improving quality of life with a wide range of benefits in individuals with chronic terminal diseases.

18 Claims, 7 Drawing Sheets

Fig. 7

BIOCOMPOSITION STIMULANT OF THE IMMUNE SYSTEM, ANTI-TUMOR AND ANTI-HIV

This is a National Phase Application filed under 35 U.S.C. 371 as a national stage of PCT/EC2008/000007, filed on Sep. 18, 2008, an application claiming the benefit under 35 U.S.C. 119 of Ecuadorian Application No. SP07-7765, filed on Sep. 21, 2007, the content of each of which is hereby incorporated by reference in its entirety.

TECHNICAL FIELD

The invention refers to a herbal composition, more specifically, a composition that can be used to promote healthy function of the prostate in men, and to help in the treatments of chronic and degenerative diseases caused by malignant tumors. The technical field to which this invention is directed is the pharmaceutical area and medicine.

BACKGROUND

Medical Background

Prostate tumors are the second cause of death for men. 40% of men over 50 years of age show symptoms associated with the growth of this gland, which in turn constitutes the second cause of death for men.

The American Cancer Society reports 230,110 new cases of prostate cancer in the United States (2004 report) with a mortality of 29,900 patients a year. It is calculated that this figure might reach the number of 27,050 deaths in 2007.

The conventional treatment include: radical prostatectomy, or denervation of the gland, external radiation, x-ray of seed, cryotherapy, hormone therapy, each one entailing collateral effects and other limitations. Anyhow, in the long term, all of them lead to a recurrence of the cellular growth.

A quick test to diagnose an alteration at the prostatic gland level is the Prostate Specific Antigen (PSA), also useful as a parameter to follow-up the disease progression. This marker is produced by both, healthy tissue and diseased tissue as well. The normal range is between 0 and 4 ng/ml. A value over 4 constitutes a clear alert of Benign Prostatic Hyperplasia, prostatitis or the beginning of a cancerous tumor. High PSA values are directly related to the seriousness of a malignant tumor of the gland.

The prostatic gland may suffer several disorders including prostatitis and Benign Prostatic Hyperplasia, causing inflammation and enlargement of the gland, resulting in very uncomfortable symptoms: difficulties with the normal flow of urine, at the beginning, at the end, interruption, a sense that the bladder does not empty, urinary urgency or frequency, specially at night, and frequent and continuous low back pain.

Existing drug therapy can reduce symptoms, but with significant side effects such as impotence and damage to liver function. Recent studies by the National Academy of Sciences show that enzyme 5-lipoxygenase is involved in the proliferation of prostate cancer cells, inhibition of this enzyme leads to rapid apoptosis of these cells but with significant side effects including eosinophilia, cardiomyopathy, and liver injury.

In addition to drug therapies, there are other therapeutic alternatives. Several international studies suggest that ginger contains constituents that may inhibit the 5-LO (5-lipoxygenase) U.S. Pat. No. 5,763,673; Chem. Phar. Bull (Tokyo) 1992 February; 40 (2):387-91. Inhibition of prostaglandin and biosynthesis by leukotrien and gingerol and diarylheptanoids, Kiuchi, F. Iwakuni S. Shibuya M. Hanoka F, Sankawa U Faculty of Pharmaceutical Sciences, University of Tokyo, Japan, Nipon Yakurigaku Zasshi 1986 October; 88 (4): 263-9 Pharmacological studies on Ginger IV Effect of (6) shogaol on the Arachidonic cascade. Suekasa M et al.

Olive oil also has the ability to inhibit 5-LO. Bioscience, Biotechnology, 1997 February 61 (2) 347-50 Inhibition of arachidonate lypoxygenase activities by 2-(3,4-dihydroxyphenyl ethanol, aphenolic compound from olives. Kohyan N, Nagata T, Fujimoto S, Sekiya K, Shikoku National agricultural Experiment station, Kasagawa, Japan and Biochem Pharmacol 199 Feb. 15; 57(4): 445-9 Inhibition of leukocite 5 lypoxinesa by phenolics from olive oil, de la Puerta R, Ruiz, Hoult J R Pharmacology Group, Kings College London UK.

The extract of nettle root and its phenol component, the caffeic acid, have the ability to inhibit 5-LO, Arzneimittelforschung 1996 January; 46 (1):52-6 Anti-inflammatory effect of Urticaria dioica folia extract in comparison to caffeic malic acid, Obertreis B, Giller K, Teucher T, Behnke B, Schmitz H Strathmann A. G. Hamburg.

Many recent studies in cancer therapy have increasingly led towards finding other treatment options other than drug therapies, as these have caused severe side effects, in some cases worse than the disease itself.

Background Related to Medicinal Plants

*Kalanchoe Pinnata*

*Kalanchoe pinnatum* belongs to the Crassulaceae family, native to Madagascar. The *Kalanchoe pinnatum* is the only species found in South America, however, 200 other species of *Kalanchoe* are found in Africa, Madagascar, China and Java. The indigenous peoples of the Amazon use it for many purposes, among others, inflammation, cancer treatment and as analgesic.

In the state of the technique, there are approximately 289 patent applications related to different species of *Kalanchoe*.

*Solanum dulcamara*

*Solanum dulcamara* belongs to the Solanaceae family. It can be found in temperate zones of Asia, the Americas and Europe and it is also common in the Iberian Peninsula and Balearic Islands. It grows spontaneously from the sea to the mountains, in humid places, on the banks of streams, in the weeds, in mushrooms and walls. It likes very moist wooded areas near water.

*Solanum dulcamara* is used to treat pneumonia, bronchitis, jaundice, venereal diseases, myalgia, muscle spasms, inflammation, hypertension, cancer, etc., as well as a cleanser, laxative, diuretic, diaphoretic, sedative, and analgesic, among other illnesses.

In the state of the technique there are patent applications related to *Solanum dulcamara*; such as: U.S. 2005/0147701. Date of publication: Jul. 7, 2005. It refers to methods and compositions used for the treatment of prostate cancer. BIRM is an extract of *Dulcamara*-solanaceae associated with the treatment of CaP. The formulation is a natural remedy for a variety of diseases including HIV-1 infections and cancer.

The scope of protection of this patent application is the method of treating a mammal with prostate cancer which comprises administering an effective amount of BIRM.

BIRM is an extract of *Dulcamara*-solanaceous and bioorganic minerals, such as: calcium, magnesium, aluminum, iron, manganese, silicon and zinc.

RU 2 211 045. Date of publication: Aug. 27, 2003. It refers to homeopathic agents used to treat skin diseases, psoriasis, and eczema. These agents are: *Dulcamara solanum, Lycopodium clavatum, Nux vomica* and *Rhus toxicodendron*.

RU 2 209 076. Date of publication: 27, 2003. It refers to a method for preventing and treating bacterial and viral diseases of poultry, for which homeopathic substances are administered in pellets containing Lachesis C 6, Echinacea C6, Aconitum C12, Bryonia C 6, C 12 and Beladonna C 12 and for weakened poultry it is necessary to previously introduce homeopathic substances containing Aconitum C 12, *Dulcamara* C 6, Natrium carbonicum C 30.

RU 2 162 334. Date of publication: Jan. 27, 2001. It refers to homeopathic drugs for the treatment of patients with osteoarticular diseases (osteoarthritis, osteochondrosis, arthrosis, arthritis). This composition has the following components: Berberis vulgaris, calcium phosphate, *Dulcamara solanum, Rhus toxicodendron* and caustic soda.

GB 1 457 968. Date of publication: Dec. 8, 1976. It refers to a process to obtain a mineralized water solution. It also refers to a composition of a quantitatively mineralized water solution containing ions (potassium, lithium, calcium, ammonium, magnesium), anions (carbonate, lactate, chlorates, bicarbonates, acetates) and un-dissociated substances such as lactose, fluid extracts of fresh urginea soilla urginea plants, Colchicum autumnale, stigmata maidis, *Solanum dulcamara,* and *sambucus pigra.*

DE 2011730. Date of publication: Feb. 25, 1971. It refers to unique plants *Solanum dulcamara* L., rich in tomatidine. These plants are first selected and isolated by keeping such selection and isolation from the next generation, continuing until the chemical species that carries tomatidine oil is chemically uniform and homozygous. In this way, the harvest is adequate and the plant is more readily available for the pharmaceutical industry.

GB 608, 596. Date of publication: Sep. 17, 1948. It relates to a method of medicine preparation which involves making a vaccine that contains germs taken from human mucous membrane in order to multiply in a solid environment; in addition, it contains *Dulcamara* among other components.

*Solanum lyratum*

*Solanum lyratum* belongs to the Solanaceae family. It is located on hills and low mountains of Japan.

This plant is used as depurative, leucorrhoea, abscesses, esophagus and stomach cancer.

In the state of the technique, there are patent applications related to *Solanum lyratum:* CN101073636, CN1589815, CN1241427, CN1186679, CN1152446, CN1104898, CN1093270, CN1077122, JP3127736, JP63202357 and JP63201130, all related to the combination of *Solanum lyratum* with other medicinal plants used as anti-tumor and to strengthen the immune system, with the exception of the last two patents that do not relate to combinations of medicinal plants but to the provision of an anti-tumor agent containing the extract of *Solanum lyratum* as a single active component.

*Solanum laciniatum*

*Solanum laciniatum* belongs to the Solanaceae family. There are 117 species in Australia, 87 of which are endemic. These plants are considered as a source of steroids, important for the pharmaceutical industry.

In the state of the technique there are two patent applications: GB 1108656 related to a *Solanum* alkaloid isolation process out of *Solanum* plants. This process involves extracting the alkaloids from the plant with an aqueous solution containing sufficient amount of a reducing agent, and; GB 1128336 which also relates to recovery procedures of physiologically active substances of *Solanum laciniatum.*

*Bryophillum calycinum*

*Bryophillum calycinum* belongs to the family of Crassulaceaes. It is a native plant of Tropical Africa.

This plant is used in popular medicine to treat wounds, bruises, burns, abscesses and respiratory tract problems (such as: cough, sore throat, inflammations), bruising, glaucoma, etc.

*Kalanchoe farinacea*

*Kalanchoe farinacea,* belongs to the family of Crassulaceaes. This is an endemic plant of Socotra Island which is located two hundred and fifty miles away from the coast of Yemen. Its natural habitat is the scrubland that grows from 100 to 800 meters high, and can be found in tropical and subtropical areas.

DETAILED DESCRIPTION OF THE INVENTION

In the state of the technique, previous patent applications do not show herbal compositions containing *Kalanchoe pinnata, Solanum dulcamara, Solanum lyratum, Solanum laciniatum, Bryophillum calycinum, Cotyledon calycina, Bryophillum daigremontiana* and *Kalanchoe farinacea.* In this sense, this invention shows another alternative for cancer treatment with greater efficiency and without known side effects.

The invention refers to the development of a special composition of plants taken from undomesticated wild sources through their meristem. It also refers to their extracts obtained from improved processes where these extracts, along with their active principles, generate synergies showing characteristics such as: anti-inflammatory, antiviral nutritional supplement, stimulant of the immune system. It also promotes prostate health and the basis to improve the quality of life facing a wide range of benefits for individuals suffering from terminal chronic diseases, especially caused by tumors.

Through this composition not only we provide an herbal composition able to promote prostate health but also it allows a synergy effect. It also includes injury prevention, maintains a quality sexual function, works as an antioxidant and avoids undesirable side effects.

Additionally, the vast majority of individuals with chronic diseases require dietary supplements, appetite stimulation, and improvement of the quality of life, especially when dealing with maintaining an adequate immune level to fight against any opportunistic pathology during the survival period considering their prognosis, which can be achieved with this herbal composition.

The first objective of the invention is to provide an herbal composition, more particularly, a composition that can be used to promote healthy prostate function in men as well as to help in the treatment of chronic and degenerative diseases caused by malignant tumors.

In accordance with this invention, the inventors provide an herbal composition containing *Kalanchoe pinnata, Solanum dulcamara, Solanum lyratum, Solanum laciniatum, Bryo-*

*phillum calycinum, Cotyledon calycina, Bryophillum daigremontiana* and *Kalanchoe farinacea* where they act in synergy. This composition is useful not only as a nutritional supplement that promotes appetite but also stimulates the immune system response. In addition, it shows anti-inflammatory properties in mammals.

In this invention process, a group of plants was specifically chosen and combined considering their biological activity. Every component of the plant has been previously characterized and evaluated. Thus, the active principles involved are: arachidonic acid, talar, beta sitosterol, briofilenona, briophyllum A, briophyllum C, briophyllol, bufadienolides, caffeic acid, campestrol, cinnamic acid, clionasterol, codisterol, epigallocatechin, flavonoids, glutinol, oxalic acid, oxaloacetate, palmitic acid, patulin, protocatechuic acid, pseudotaxasterol, quercetin, rutin betulinic acid, stigmasterol, succinic acid, taraxerol, solanine, dulcamarina, soladulcinina.

Similarly, the concentration of each component of the herbal composition has been determined so as to achieve the desired therapeutic benefits. In the herbal composition of the invention, the weighting coefficient of *kalanchoe* has been defined as 1, keeping direct consideration to the other plant's weighting coefficient also of 1:0.5 to 8, where the *dulcamara* can be 1 to 4 and the other remaining plants 1 to 8.

The *Kalanchoe* has the largest number of metabolites and it is these metabolites that react with other plant's resulting in a synergy effect of the claimed composition. In other words, the plants that are part of the herbal composition, in a separate way, produce few therapeutic effects. In combination with *kalanchoe* the therapeutic effect of all plants is increased.

The combination to make it work as a stimulant of the immune system plus the criterion of nutritional supplement and the antioxidant capacity is a new concept. The selected plants have the following biological activities: anti-inflammatory, anti-tumor, immune system activator, anti-viral. The qualities of the plants used in this invention have been partially reported in scientific studies. Many of them have multifunctional activity.

All the benefits of the herbal composition of this invention have been demonstrated through biological tests performed in patients with prostate cancer with node metastases and invasion of the bladder floor, female patients diagnosed with ductal in situ cancer with brain metastasis, patients with AIDS, etc. These tests are described below.

A second objective of the invention is to provide a manufacturing process of an herbal composition that involves the following steps:
a) Obtaining fresh plants that have been developed by meristems of wild plants.
b) Obtaining an alcoholic or aqueous extract from fresh plants obtained as indicated in letter a) above, using the proper solvent.
c) Dehydration of alcoholic or aqueous extracts, for which purpose extracts undergo temperatures between 40 to 70 degrees Celsius for a period of time between 15 to 50 minutes.
d) Second dehydration process of alcoholic or aqueous extracts at temperatures between 30 to 70 degrees, eliminating the excess solvent to further add conventional substances for the preparation of the herbal composition.
e) Pulverization of alcoholic or aqueous extracts.
Steps a) to e) are followed for every plant that is part of the herbal composition.
f) Mixture of the powdered substances obtained from alcoholic or aqueous extracts of each plant.
g) Mixture of the powdered substances indicated in letter f) with other helping components that may be chosen from among: ascorbic acid, paraben, flavors, xanthan gum.

Prior to this process, tests are carried out to the *Solanum dulcamara* to ensure proper utilization of the correct species, that is, the one with the therapeutic benefits. For this purpose, it is necessary to seek the presence of alkaloids through trials like Dragendorff's and the utilization of Mayer's reactive. Refer to Table No. 1, Exhibit 1 and Chromatographic Plates A (left) and B (right), FIG. 1, Exhibit 2.

All steps of the production process have been determined so that existing problems are solved and technical advantages are brought to the process, thus, maintaining temperature levels between 40 to 70 degrees Celsius considering that these temperatures are optimal to achieve the synergy effect of the herbal composition. On the other hand, if the extracts undergo temperatures above 70° C. alterations of metabolites may result. Besides, if dehydration of the extract exceeds 50 minutes, the active principle may disappear. Such is the case of the *Bryophillum calycinum* which denaturalize.

This process is executed following all the quality standards of good manufacturing practices.

For a better understanding, following are several examples of the way this invention was carried out, without limiting its scope of protection.

Example No. 1

Preparation of the Composition

The preferred formulation of the invention's composition is executed with *kalanchoe pinnata, solanum dulcamara, solanum lyratum, solanum laciniatum, bryophillum calycinum, cotyledon calycina, bryophillum daigremontiana* and *Kalanchoe farinacea*.

The alcoholic or aqueous extract was prepared by processing fresh plants developed by meristems from wild plants, dehydrating them for their further pulverization and mixture according to the invention's statements.

The weight coefficient of *kalanchoe* is 1 and the relationship with other plants might be 1:0.5 to 8.

Example No. 2

Preparation of the Herbal Solution

It is produced following the usual steps of the process for the preparation of herbal solutions of the state of the technique. The difference is that the solution undergoes temperatures between 40 to 70 degrees Celsius. These temperatures are considered optimal to achieve the synergy effect of the herbal composition, during 15 to 50 minutes.

A second dehydration process of the alcohol or aqueous extracts is executed, at temperatures between 30 to 70 degrees, eliminating the excess of solvents to further add conventional substances for the preparation of the herbal composition.

The following biological examples illustrate the beneficial action of the composition on organisms subject to harmful factors whether artificially or naturally, without limiting its future application meant to be applied in different primary or metastatic tumors.

Example No. 3

Anti-Inflammatory Activity 6 rabbits weighing 400 grams were used. Each one was applied 0.1 cc. of croton oil to the external ear producing the expected inflammatory reaction, consisting in an edema and vascularization of the injured area. The reaction of the skin of the affected area with increased vascularization occurred in 1 hour. The worst effect appeared in 6 hours causing an 8 mm edema.

The injury without treatment returns to normal after 4 days. 0.5 cc. of the composition was injected in the affected area, on three occasions: immediately, 1 hour after the aggression, and 6 hours after the injury.

The Result was:

During phase 1, there was a 50% recovery of the injury after three hours from the application of the composition, and total tissue recovery after nine hours (the edema disappears and the vascularization is almost non-existent). When the composition is applied after an hour the injury occurred, the edema reduces by 40%. 5 hours later. This is because of the toxicity of the croton and the establishment of its effects on the mammal's tissue.

Example No. 4

Clinical Observation

The patient is a 73 year old individual diagnosed with prostate cancer with node metastases and invasion of the bladder floor. The body bone scan with 99m TC-MDP does not show injuries. In March 2003, PSA level was 1096, the carcinoembryonic antigen was 6.85.

Carcinoembryonic antigen is a substance that usually only appears during fetal development and reappears again in adults who develop certain types of cancer: colon, rectum, stomach, esophagus, liver, pancreas, bladder, and breast (female mammary gland), lung and prostate as well.

The test of carcinoembryonic antigen (CEA) plays an important role in monitoring patient outcomes with cancer and metastasis. Even though it can not be considered a final marker, it serves as a useful guide. Its constant increase means that therapy has not achieved positive results. A decrease indicates a trend towards regression of the lesion.

The patient starts with a daily dose of 250 mg of Flutamide (fluxus) until reaching a PSA of 252. After 4 months, PSA reaches 525. From this point, the patient receives a double dose of Flutamide until registering a PSA of 256. CEA level was 5.84. After three months PSA rises again to 580. The tumor becomes resistant to hormone therapy. Considering the patient's refusal to continue with conventional therapy or emasculation (castration), and after one month in which the patient does not receive any medication, the patient initiates an alternative therapy consisting in the administration of the composition of this invention, that is, 15 ml per day orally. At first, PSA level was 600 and CEA level was 8.86. After a month and a half the patient has got out of bed and has better appetite and a better mood. CEA level has dropped to 6.51. PSA level has changed to 700, a much better value if compared to the resistance to flutamide. He has not shown any side effects or allergies to the composition of the invention.

The patient underwent surgery to improve the diameter of the urethra and to remove the catheter that started to produce frequent bleeding. After the surgery, the patient suffered a massive infection due to *Escherichia coli* bacteria. He received anti-bacterial treatment with good results. PSA reached 698. After the surgery, the administration of the composition of the invention re-started, and after 2 months, PSA dropped to 88 and CEA to 5.04. During the following 2 months, PSA level reached 10 ng/ml level. After 70 days, PSA registers 4 ng/ml levels, which are considered normal values. CEA level was 3.97. Currently, the patient has returned to work (August, 2005). He had also had dialysis due to complications during the surgery. The patient has been taking the composition in daily basis during the next two years, maintaining a good health condition. Despite the three dialysis sessions per week that he is receiving, his general state is good; he manages to do everything by himself and exercises every morning; PSA is 15 but CEA has always been 2.5 ng/ml. During these two years (March, 2007), he has kept a strict diet and has not received any other type of anti-tumor therapy.

Example No. 5

This is a female patient with a diagnosis of in situ ductal carcinoma with brain metastases. She has received chemotherapy based in Docetaxel during the last two years. Her evolution is not positive. She is currently receiving Taxol and the composition of the invention as well.

The extract inhibits the appearance of side effects associated with chemotherapy; there is no neutropenia, nausea, diarrhea or myalgia.

In this case we used as guide tumor markers, the carcinoembryonic antigen and CA 15-3.

From values as high as 77.42 ng/dl. CEA dropped to 19.04 ng/dl. in 3 months. Also, CA 15-3 dropped from 92.1 U/ml. to 32.8 U/ml. in 3 months. Refer to FIGS. 2-7.

Example No. 6

Patient diagnosed with immunodeficiency virus with a viral load of 1,156,000 and a CD4 of 336. He starts receiving the composition of the invention after antiretrovirals did not produce the expected results. After 60 days of treatment, they achieve changing CD4 to 516, CD8 to 313, thus, modifying CD4/CD8 relation to 1.65 from clearly pathological values of 0.23. The patient's general condition has improved as well as his defense level; therefore, the patient is no longer susceptible to opportunistic infections.

Advantages of the Invention

Advantages of the Herbal Composition

One of the advantages of the invention is that the herbal composition shows a synergy effect, meaning that the therapeutic effects of the herbal composition increase because of the *Kalanchoe* action, which has the highest level of metabolites. These metabolites react with that of the other plants resulting in the synergy effect of the composition, as evidenced in the biological studies described above.

Another advantage of the invention is that it provides a composition that allows a normal cell activity as well as vitality in degenerative cases, supporting in an important manner, the prostate health and providing quality sexual function.

Another advantage of the composition is that in addition to the above mentioned, it has antioxidant benefits.

A further advantage is to provide methods of applying the composition with active principles that administered in different ways causes beneficial therapeutic effects without undesirable side effects.

Another advantage is that the composition administered to humans achieves an improved level of body's defenses, especially against immunodeficiency virus.

Advantages of the Preparation Process of the Herbal Composition

One of the advantages of the process compared to conventional processes of the state of the technique, is that all phases of this preparation process have been determined so that existing problems have been solved, adding technical advantages to the process; thus, temperature levels between 40 to 70 degrees Celsius are kept, considering that these are the optimum levels to achieve the herbal composition's synergy effect. On the other hand, if extracts are subject to temperatures above 70° C. it may cause an alteration of metabolites and if the extract dehydration exceeds 50 minutes, the active principle may disappear, as is the case of *Bryophillum calycinum* which denaturalizes.

Exhibit 1

Detection of Alkaloids in *Solanum dulcamara* Through Trials Like Dragendorff's and Mayer's Reactive:

TABLE 1

|  | Aqueous Extract FT01 | Aqueous Extract DNS01 and KP001 | Ethanolic Extract DNS01 and KP001 | Control |
|---|---|---|---|---|
| Mayer Dragendorff | Turbidity Red brick precipitate (Pos) | Turbidity Red brick precipitate (Pos) | Turbidity Red brick precipitate (Pos) | No turbidity No precipitate |

Discussion:

For Mayer and Drafendorff, the positive reaction indicates the presence of alkaloids in both, DNS01/10001 alcoholic and aqueous extracts, as shown in reference sample FT001.

This is only a qualitative test.

Exhibit 2

Figure 1:
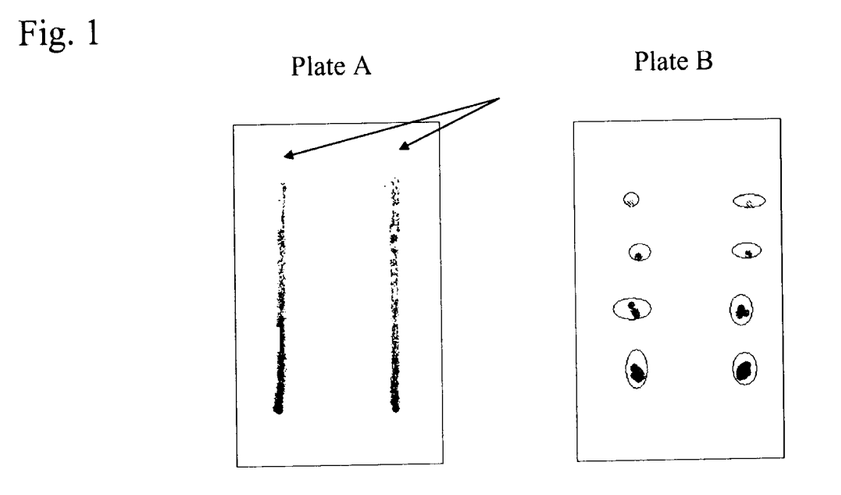
FIG. 1 is a chromatographic plate comparison of FT001 and the aqueous mixture of DNS01 and KP001, consisting of chromatographic plate A (left) and chromatographic plate B (right).
Figure 2:
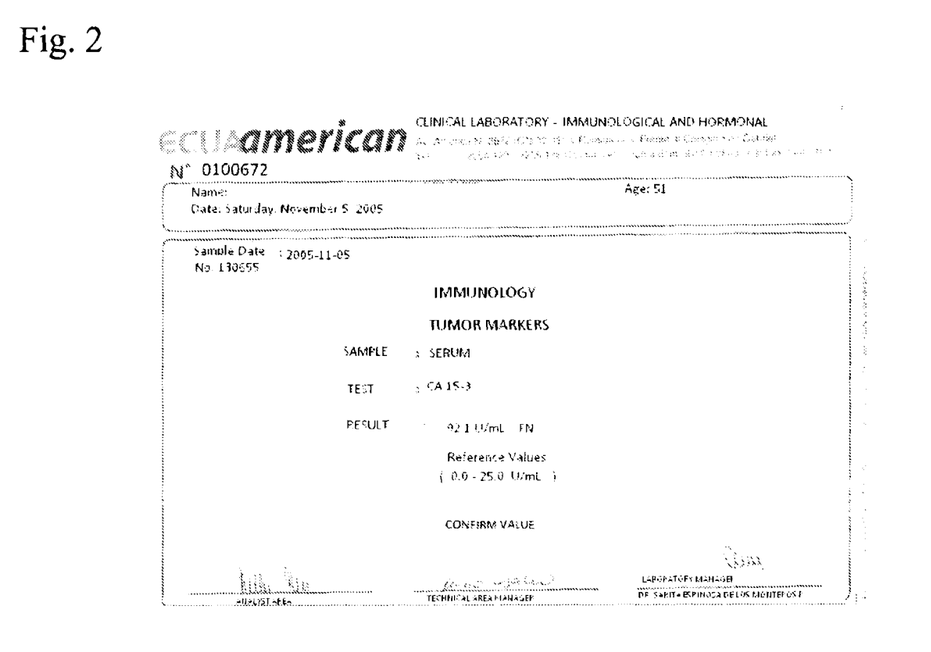
FIG. 2 is a CA 15-3 Immunology Tumor Markers Test dated Nov. 5, 2005.
Figure 3:
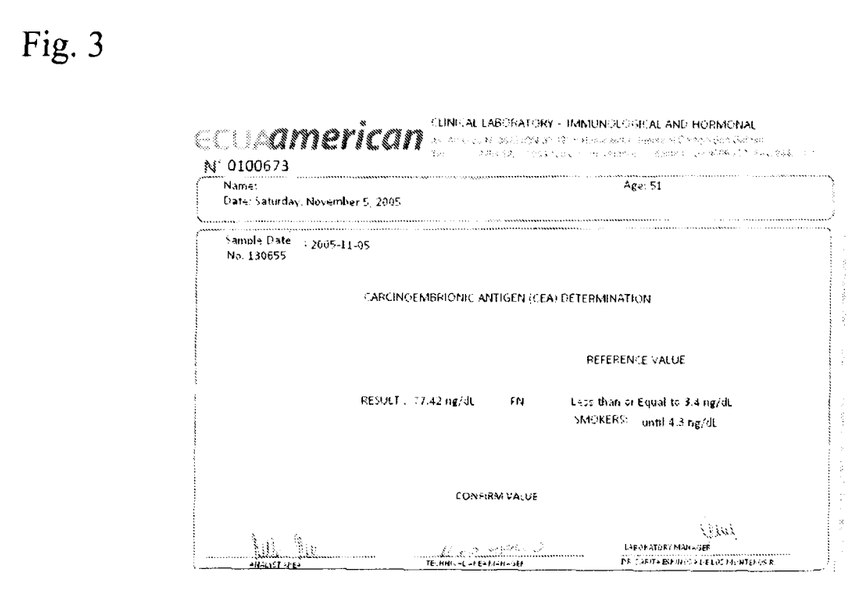
FIG. 3 is a Carcinoembrionic Antigen (CEA) Determination dated Nov. 5, 2005.
Figure 4:
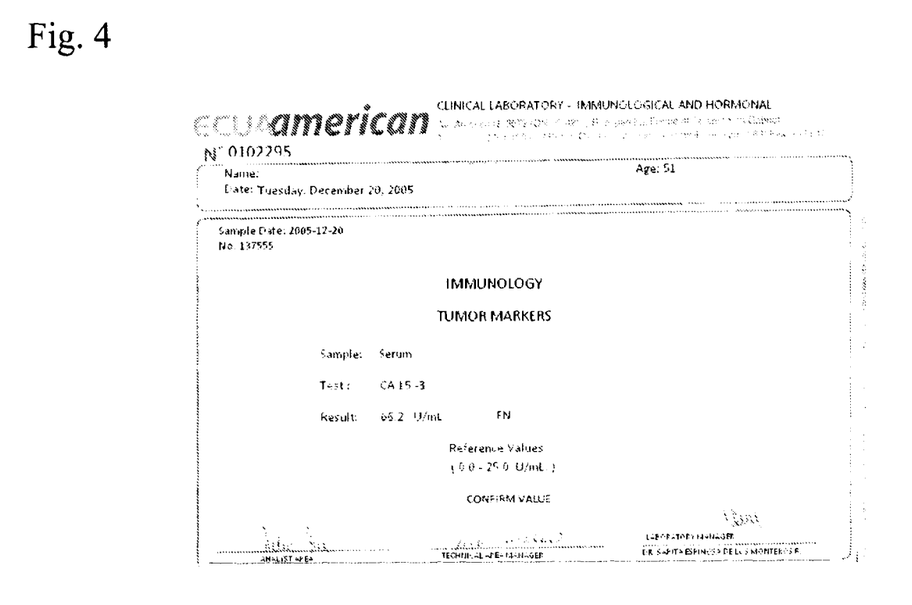
FIG. 4 is a CA 15-3 Immunology Tumor Markers Test dated Dec. 20, 2005.
Figure 5:
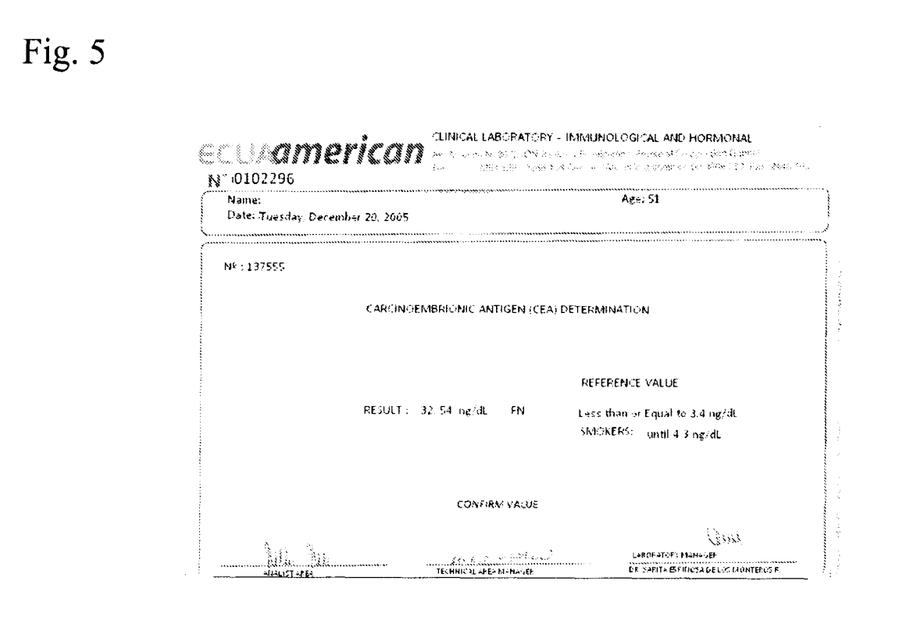
FIG. 5 is a Carcinoembrionic Antigen (CEA) Determination dated Dec. 20, 2005.
Figure 6:
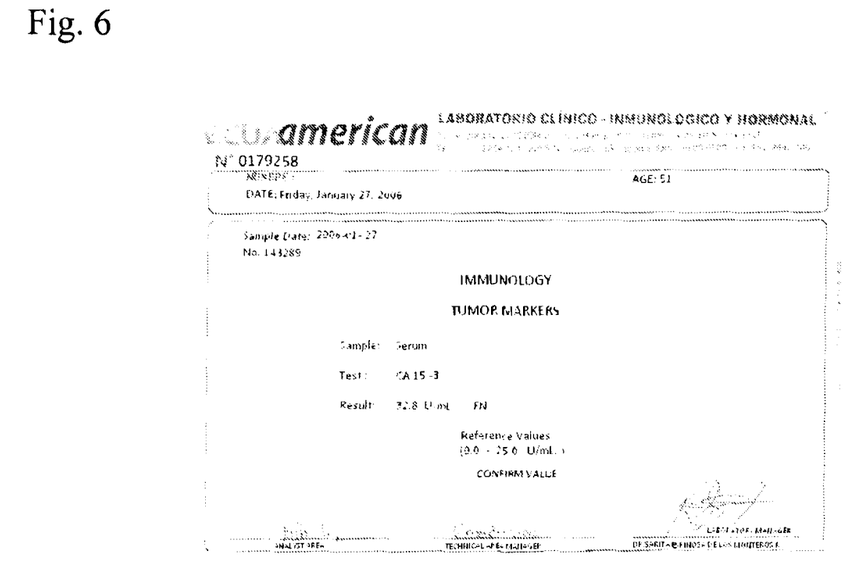
FIG. 6 is a CA 15-3 Immunology Tumor Markers Test dated Jan. 27, 2006.
Figure 7:
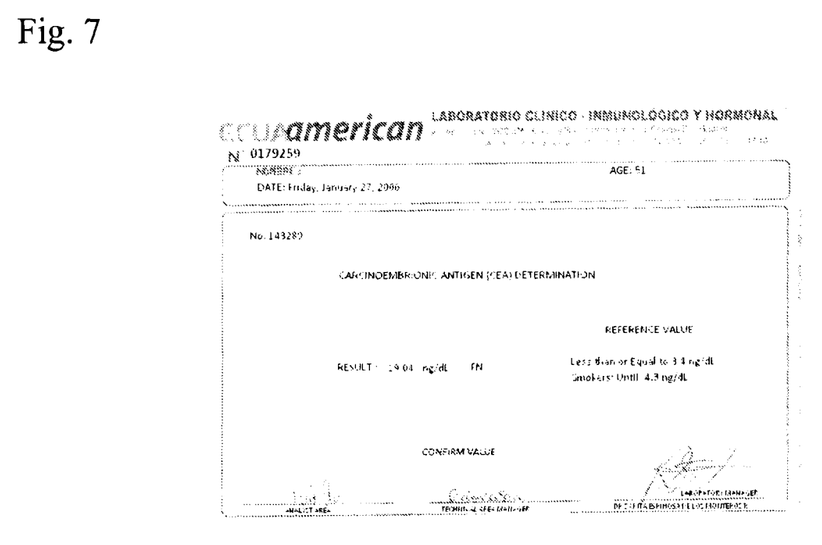
FIG. 7 is a Carcinoembrionic Antigen (CEA) Determination dated Jan. 27, 2006.

Chromatographic Plates of the Herbal Composition:
Refer to FIG. 1.
Analysis:

According to the chromatography we can indicate that the DNS01 and KP001 aqueous mixture is very similar to the FT001 chromatogram shown. Probably, such differences are due to additives or other components of the FT001.

The same conclusion can be reached if the different peaks of the infrared spectra are analyzed. The similarity between the FT001 spectrum and the mixture is very high. An 80 to 90% similarity could be estimated as possible value.

One could also say that the reference of the FT001 has a higher concentration of almost all its components, thus, it is necessary to prepare a more concentrated extract.

The chromatography of alcoholic and aqueous extracts showed that the two processes have the same extraction capacity even though in the ethanolic extract a darker color was obtained, possibly because some other components are extracted from the plant. The disadvantage is that besides raising the production costs, it gives somewhat unpleasant organoleptic properties.

Exhibit 3

Microbiological Tests to Determine Bactericidal Properties of the Aqueous and Ethanolic Extracts of the Composition of the Invention:

TABLE 2

Microbiological results

|  | Aqueous Extract | Ethanolic Extract | FT001 | Control |
|---|---|---|---|---|
| *S. aureus* | With inhibition halo | Without inhibition halo | With inhibition halo | With inhibition halo |
| *P. auriginosa* | Without inhibition halo | Without inhibition halo | Without inhibition halo | N/A |
| *C. albicans* | Without inhibition halo | Without inhibition halo | Without inhibition halo | N/A |

Analysis:

The microbiology results showed that the ethanol extract has no inhibitory properties to *Staphylococcus aureus*. This table shows that both the FT001 and the aqueous extract have antimicrobial properties against *S. aureus*. It has to be mentioned that the halos were compared with the lower standard of Gentamicin corresponding to 2 µg/ml. equivalent to a 12.2 mm. halo, while the aqueous extract halo was diffuse and had an equatorial zone of 11 mm. The inhibitory halo of FT001 registered a diameter of approximately 12 mm.

The invention claimed is:

1. A synergistically active composition of plant extracts comprising:
    *Kalanchoe pinnata* plant extract in proportion to a mixture of *Solanum dulcamara, Solanum lyratum, Solanum laciniatum, Bryophillum daigremontiana* and *Kalanchoe farinacea* plant extracts, based on a dry weight, ranging from 1:0.5 to 1:8;
    said mixture comprising between 1 to 4 parts of the *Solanum dulcamara* plant extract and between 1 to 8 parts of each of *Solanum lyratum, Solanum laciniatum, Bryophillum daigremontiana* and *Kalanchoe farinacea* plant extracts.

2. The composition of claim 1, wherein the plant extracts comprise one or more active agents selected from the group consisting of arachidonic acid, astragalin, beta sitosterol, briofilenona, briophyllum A, briophyllum C, briophyllol, bufadienolides, caffeic acid, campestrol, cinnamic acid, clionasterol, codisterol, epigallocatechin, flavonoids, glutinol, oxalic acid, oxaloacetate, palmitic acid, patulin, protocatechuic acid, pseudotaxasterol, quercetin, rutin betulinic acid, stigmasterol, succinic acid, taraxerol, solanine, dulcamarina and soladulcinina.

3. The composition of claim 1, wherein the composition is provided in an oral formulation selected from the group consisting of capsules, elixirs, granules, suspensions, syrups, food additives, powder beverages and tablets; or a formulation for inhalation administration, said formulation comprising a therapeutically effective amount of the composition.

4. The composition of claim 3, for treatment of a condition selected from the group consisting of breast cancer, prostate cancer, acquired immunodeficiency disease, inflammation, and a side-effect caused by chemotherapy treatment.

5. The composition of claim 4, for the treatment of breast cancer, prostate cancer, and/or acquired immunodeficiency disease.

6. The composition of claim 4, for the treatment of inflammation.

7. The composition of claim 4, for the treatment of a side-effect caused by chemotherapy treatment.

8. The composition of claim 7, wherein the side-effect is selected form the group consisting of neutropenia, nausea, diarrhea and myalgia.

9. The composition of claim 1, further comprising at least one adjuvant selected from the group consisting of ascorbic acid, parabens, flavors, xanthan gum and mixtures thereof.

10. The composition of claim 9, wherein the composition is provided in an oral formulation selected from the group consisting of capsules, elixirs, granules, suspensions, syrups, food additives, powder beverages and tablets; or a formulation for administration via inhalation, wherein the composition comprises a therapeutically effective amount of the composition.

11. The composition of claim 10, for the treatment of a condition selected from the group consisting of breast cancer, prostate cancer, acquired immunodeficiency disease, inflammation, and a side-effect caused by chemotherapy treatment.

12. The composition of claim 11, for the treatment of breast cancer, prostate cancer, and/or acquired immunodeficiency disease.

13. The composition of claim 11, for the treatment of inflammation.

14. The composition of claim 11, for the treatment of a side-effect caused by chemotherapy treatment.

15. The composition of claim 14, wherein the side-effect is selected from the group consisting of neutropenia, nausea, diarrhea, and myalgia.

16. A method for treatment of a condition selected from the group consisting of breast cancer, prostate cancer, acquired immunodeficiency disease, inflammation, and a side-effect caused by chemotherapy treatment comprising:
   administering to a subject in need thereof, a therapeutically effective amount of the composition of claim 1.

17. The method of claim 16, wherein said administering comprises oral administration.

18. A process for preparing the synergistically active composition of claim 1, comprising:
   a) obtaining a fresh plant that has been developed by meristems of a wild plant, the fresh plant selected from the group consisting of *Kalanchoe pinnata, Solanum dulcamara, Solanum lyratum, Solanum laciniatum, Bryophillum daigremontiana* and *Kalanchoe farinacea;*
   b) preparing an aqueous or alcoholic extract from the fresh plants obtained in step a), using a suitable solvent;
   c) dehydrating the alcoholic or aqueous extracts at a temperature of from 40° C. to 70° C. for a period of time from 15 to 50 minutes to produce a first dehydrated extract;
   d) dehydrating the first dehydrated extract at a temperature of from 30° C. to 70° C., and removing excess solvent, to produce a dehydrated extract;
   e) pulverizing the dehydrated extract to produce a pulverized extract;
   f) mixing the pulverized extract from each plant to produce a pulverized mixture, the pulverized mixture comprising *Kalanchoe pinnata* plant extract in proportion to a mixture of *Solanum dulcamara, Solanum lyratum, Solanum laciniatum, Bryophillum daigremontiana* and *Kalanchoe farinacea* plant extracts, based on a dry weight, ranging from 1:0.5 to 1:8, wherein said mixture comprises between 1 to 4 parts of the *Solanum dulcamara* plant extract and between 1 to 8 parts of each of *Solanum lyratum, Solanum laciniatum, Bryophillum daigremontiana* and *Kalanchoe farinacea* plant extracts; and
   g) adding one or more components selected from the group consisting of ascorbic acid, parabens, flavors, and xanthan gum, to the pulverized mixture.

* * * * *